United States Patent [19]

Fujino et al.

[11] Patent Number: 4,476,051

[45] Date of Patent: Oct. 9, 1984

[54] METHOD FOR PROTECTING AMINO GROUP AND RESTORING THE SAME

[75] Inventors: Masahiko Fujino, Takarazuka; Mitsuhiro Wakimasu, Suita, both of Japan

[73] Assignee: Takeda Chemical Industries, Ltd., Osaka, Japan

[21] Appl. No.: 436,691

[22] Filed: Oct. 26, 1982

[30] Foreign Application Priority Data

Oct. 29, 1981 [JP] Japan .................................. 56-174125

[51] Int. Cl.$^3$ ........................................... C07C 103/52
[52] U.S. Cl. ............................................ 260/112.5 R
[58] Field of Search .................. 260/112.5 R; 562/430

[56] References Cited

U.S. PATENT DOCUMENTS 3,997,516 12/1976 Nishimura .................... 260/112.5 R
4,368,150 1/1983 Fujino et al. ........................ 562/430

FOREIGN PATENT DOCUMENTS 33976 8/1981 European Pat. Off. ...... 260/112.5 R

OTHER PUBLICATIONS

Chem. Pharm. Bull. 29, 10, 2825–2831 (1981).
J. C. S. Chem. Comm. (1980) 668–669.
J. Chem. Soc. Chem. Comm. (1982) 445–446.
Chem. Pharm. Bull. 29, 9, 2592–2597 (1981).

*Primary Examiner*—Delbert R. Phillips
*Attorney, Agent, or Firm*—Wenderoth, Lind & Ponack

[57] ABSTRACT

An ω-amino group and/or α-amino group in an amino acid or a peptide can be protected with a 4-methoxy-2,3,6-trimethylbenzenesulfonyl group, and said group may easily be removed without affecting the amino acid or the peptide. Thus, the present invention is useful in the synthesis of peptide containing ω-amino group and-/or α-amino group.

5 Claims, No Drawings

METHOD FOR PROTECTING AMINO GROUP AND RESTORING THE SAME

This invention relates to a method of producing peptides which uses amino acids with their ω-amino group and/or α-amino group protected with a 4-methoxy-2,3,6-trimethylbenzenesulfonyl group as well as such amino-protected amino acids or peptides, and salts thereof.

In the production of peptides, protection of the ω-amino group or α-amino group is generally required. In the case of the ω-amino group in diamino acids (e.g. lysine, ornithine, α,γ-diaminobutyric acid, α,β-diaminopropionic acid), this is particularly important, since selective cleavage of their ω-amino-protecting groups is required, without affecting their α-amino-protecting groups. So far, a carbobenzoxy group, which is stable to acids such as trifluoroacetic acid and is removable by catalytic reduction, and a tert-butyloxycarbonyl group, which can be removed with an acid, have most frequently been used as the ω-amino group-protecting groups. However, the synthesis of complicated peptides cannot be performed in a satisfactory manner with the above two protective groups alone. A protective group stable against both treatment with an acid such as trifluoroacetic acid and catalytic reduction but removable in a mild acidic condition in the last step has been much desired. Diisopropyloxycarbonyl and p-methylbenzylsulfonyl groups are known to be stable against both treatment with an acid such as trifluoroacetic acid and catalytic reduction. However, the use of a strong acid such as anhydrous hydrogen fluoride is essential for the removal of these protective groups. The use of anhydrous hydrogen fluoride is undesirable from the industrial viewpoint. Among protective groups of the benzenesulfonyl type, p-toluenesulfonyl has also been used for the protection of the ω-amino group of lysine. However, this protective group is disadvantageous in that it can be removed only by treatment with sodium in liquid ammonia but is very stable to treatment with various acids.

The present inventors studied various protective groups of the substituted benzenesulfonyl type and as a result have found that 4-methoxy-2,3,6-trimethylbenzenesulfonyl can be removed by mild acid treatment. Further research based on this finding has led to completion of the present invention.

Thus, the invention provides (1) a method of producing peptides having an ω-amino group and/or α-amino group which comprises protecting the ω-amino group and/or α-amino group of an ω-amino group and/or α-amino group-containing starting compound with a 4-methoxy-2,3,6-trimethylbenzenesulfonyl group and, after peptide condensation reaction, eliminating said protective group with an acid and (2) amino acids or peptides, or salts thereof, with their ω-amino group and/or α-amino group being protected with a 4-methoxy-2,3,6-trimethylbenzenesulfonyl group.

The 4-methoxy-2,3,6-trimethylbenzenesulfonyl group used in accordance with the invention is a novel protective group and generally used in the form of a halide, which can be prepared, for example, by the method of Reference Example 1.

In accordance with the invention, the amino acids with their ω-amino group and/or α-amino group being protected with a 4-methoxy-2,3,6-trimethylbenzenesulfonyl group can be produced by a conventional method, for example by reacting a 4-methoxy-2,3,6-trimethylbenzenesulfonyl halide (preferably chloride) with an ω-amino group and/or α-amino group-containing amino acid. The reaction may be carried out at a temperature adequately selected within the range of about −10° C. to +50° C., for instance, and in a solvent (e.g. water, aqueous tetrahydrofuran, aqueous dioxane, aqueous acetone, aqueous acetonitrile, aqueous dimethylformamide).

As desired, the free α-amino group of the amino acid may be protected, prior to the above reaction, in a conventional method with a known protective group, such as carbobenzoxy, p-nitrobenzyloxycarbonyl, p-methoxybenzyloxycarbonyl, tert-butoxycarbonyl, tert-amyloxycarbonyl, 9-fluorenylmethoxycarbonyl, isonicotinyloxycarbonyl, o-nitrophenylsulfenyl, 2-(p-biphenylyl)isopropyloxycarbonyl or the like.

When the amino acid is an α,ω-diamino acid, the above reaction, when conducted between a metal salt of said amino acid, preferably a copper salt, and a 4-methoxy-2,3,6-trimethylbenzenesulfonyl halide, gives a metal salt of the α,ω-diamino acid with its ω-amino group being protected with the above protective group. When the metal is removed from the salt by a conventional means (e.g. treatment with hydrogen sulfide, EDTA or a resin), an ω-protected amino acid having a free α-amino group and a free carboxyl group can be obtained.

Examples of the thus-obtainable amino acid having a 4-methoxy-2,3,6-trimethylbenzenesulfonyl-protected ω-amino group and/or α-amino group are lysine derivatives of the general formula

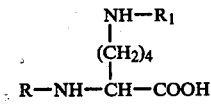

wherein at least one of R and $R_1$ is a 4-methoxy-2,3,6-trimethylbenzenesulfonyl group and the other, if any, is a hydrogen or a protective group other than a 4-methoxy-2,3,6-trimethylbenzenesulfonyl group.

The thus-obtained amino acid with its ω-amino group and/or α-amino group being protected with a 4-methoxy-2,3,6-trimethylbenzenesulfonyl group in accordance with the invention can be used very advantageously in the production of peptides which contain said amino acid, if necessary following conversion into a salt with dicyclohexylamine, cyclohexylamine, sodium or the like.

Said peptide production can be performed by any of conventional methods, such as the described in, for instance, M. Bodansky and M. A. Ondetti: Peptide Synthesis, Interscience, N.Y. 1966; F. M. Finn and K. Hofmann: The Proteins, vol. 2 (edited by H. Neurath and R. L. Hill), Academic Press Inc., N.Y. 1976; and Nobuo Izumiya et al.: Peptide Synthesis, Maruzen, 1975, for example the azide method, chloride method, acid anhydride method, mixed acid anhydride method, DCC method, active ester method, method which uses Woodward reagent K, carbodiimidazole method, oxidation/reduction method, and DCC/HONB method.

After the peptide condensation reaction, the protective group of the present invention is eliminated with an acid. The elimination can be effected by a known acid treatment method, such as the methanesulfonic acid method or trifluoromethanesulfonic acid method. Furthermore, in accordance with the invention, a new acid-treatment method which uses trifluoroacetic acid containing a small amount of methanesulfonic acid or trifluoroacetic acid can advantageously be employed. Especially when carried out in the presence of thioanisole or anisole, the elimination reaction can proceed in a very advantageous manner.

Especially when the 4-methoxy-2,3,6-trimethylbenzenesulfonyl group is used as the ω-amino group-protecting group, said group can be eliminated with a trifluoroacetic acid-thioanisole mixture containing methanesulfonic acid in a low concentration of about 0.05 M to 1 M, preferably about 0.1 M to 0.5 M. When said group is used as the α-amino group-protecting group, it can be removed not only under the above conditions but also with trifluoroacetic acid-thioanisole alone.

When the peptide contains an asparagine and/or aspartic acid residue, the protective group elimination generally may involve a succinimide-type side reaction. When a serine and/or threonine residue is present, an N→O acyl replacement may take place. The use of such a mild acid as trifluoroacetic acid or trifluoroacetic acid containing methanesulfonic acid in a diluted state in accordance with the invention can avoid side reactions such as mentioned above.

The following reference examples and embodiment examples illustrate the invention in more detail. The amino acids, peptides, protective groups, active residues and so on are indicated herein also by abbreviations according to the IUPAC-IUB Commission on Biological Nomenclature or abbreviations commonly used in the art. The following are examples: Trp: tryptophan; Lys: lysine; His: histidine; Arg: arginine; Ser: serine; Gly: glycine; Ala: alanine; Pro: proline; Thr: threonine; Gln: glutamine; Val: valine; Leu: leucine; Ile: isoleucine; Met: methionine; Tyr: tyrosine (unless otherwise stated, each of the above indicates the relevant amino acid in the L form except for Gly); Z: carbobenzoxy; Boc: tert-butoxycarbonyl; OBu$^t$: tert-butyl ester; HONB and ONB: N-hydroxy-5-norbornene-2,3-dicarboximide and ester thereof, respectively; HOBt: N-hydroxybenzotriazole; DCC: N,N'-dicyclohexylcarbodiimide; DCU: N,N'-dicyclohexylurea; Pme: pentamethylbenzenesulfonyl; Mtr: 4-methoxy-2,3,6-trimethylbenzenesulfonyl; CHA: cyclohexylamine; DCHA: dicyclohexylamine; DMF: dimethylformamide; TEA: triethylamine; THF: tetrahydrofuran; MSA: methanesulfonic acid TFA: trifuluoroacetic acid; Boc-ON: 2-t-butoxycarbonyl-oxyimino-2-phenylacetonitrile. The developing solvent systems used in the thin layer chromatography herein mentioned were as follows: $R_f^1$: chloroform-methanol-acetic acid (9:1:0.5); $R_f^2$: ethyl acetate-pyridine-acetic acid-water(60:20:6:10); $R_f^3$: chloroform-methanol-water (7:3:0.5); $R_f^4$: n-butamol-pyridine-acetic acid-water (30:20:6:24); $R_f^5$: chloroform-methanol (19:1); $R_f^6$: ethyl acetate-n-butanol-acetic acid-water (1:1:1:1).

REFERENCE EXAMPLE 1

(1) Synthesis of 2,3,5-trimethylanisole

In 100 ml of dimethyl sulfoxide were dissolved 10 g of 2,3,5-trimethylphenol and 10.4 ml of methyl iodide and the solution was ice-cooled. To this solution was added 5.6 g of 60% oily sodium hydride and the mixture was stirred for 10 hours. Water was added and the resulting mixture was extracted with ether. The ether layer was washed with water and dried over anhydrous sodium sulfate. The solvent was then distilled off to give an oily substance. Yield 12.9 g (quantitative).

(2) Synthesis of 4-methoxy-2,3,6-trimethylbenzenesulfonyl chloride

In 500 ml of methylene chloride was dissolved 4.5 g of 2,3,5-trimethylanisole and the solution was cooled to −5° C. to −10° C. A solution of 6.0 ml of chlorosulfonic acid in 400 ml of methylene chloride was added dropwise, and then the temperature was allowed to rise to room temperature. The mixture was poured into an ice—5% aqueous sodium hydrogen carbonate mixture. The methylene chloride layer was washed with water and dried over anhydrous magnesium sulfate. The solvent was then distilled off, and the residue was crystallized from n-hexane.
Yield 5.0 g (67.0%).
m.p. 56°–58° C.
Elemental analysis
Calcd. for $C_{10}H_{13}O_3SCl$:
C, 48.29; H, 5.27; S, 12.89; Cl, 14.26.
Found: C, 48.42; H, 5.21; S, 12.61; Cl, 14.25.

EXAMPLE 1

Production of H-Lys(Mtr)OH

In 300 ml of water was dissolved 54 g of Lys.HCl and the solution was heated at about 50° C. To the solution was added 116 g of powdery $CuCO_3.Cu(OH)_2$ and the mixture was refluxed for 5 hours. The insoluble matter was filtered off and washed with hot water. The filtrate and washings were concentrated to about 700 ml, 96 g of $NaHCO_3$ and a solution of 82 g of Mtr-Cl in 450 ml of acetone was added, and the mixture was stirred for 15 hours. The acetone was distilled off under reduced pressure and the crystalline residue was collected by filtration. This product was suspended in 500 ml of water, followed by addition of 56 g of EDTA-2Na. The mixture was stirred and the crystalline precipitate was collected by filtration and recrystallized from dilute acetic acid.
Yield 43.5 g (40.5%).
m.p. 224°–228° C.
$[\alpha]_D^{23}+1.1°$ (C=0.92, methanol).
$R_f^2$: 0.18.
Elemental analysis:
Calcd. for $C_{16}H_{26}O_5N_2S.\frac{1}{2}H_2O$:
C, 52.29; H, 7.41;
N, 7.62; S, 8.73.
Found: C, 52.18; H, 7.14;
N, 7.55; S, 8.70.

EXAMPLE 2

Production of Z-Lys(Mtr)OH.DCHA

In 130 ml of 1 N sodium hydroxide was dissolved 0.0 g of Lys(Mtr) and the solution was ice-cooled. To the solution were added 20.6 g of Z-Cl and 110 ml of 1 N sodium hydroxide and the mixture was stirred for about 4 hours. The reaction mixture was acidified with citric acid and extracted with ethyl acetate. The extract was washed with water and dried over anhydrous sodium sulfate. The solvent was then distilled off and the residue was dissolved in ether. To the solution was added 20 ml of DCHA and the crystalline precipitate was collected by filtration and recrystallized from MeOH.
Yield 53.4 g (72.0%).
m.p. 164°–165° C.

$[\alpha]_D^{23} +5.8°$ (C=0.86 in MeOH).
$R_f^1$: 0.72.
Elemental analysis:
Calcd. for $C_{24}H_{32}O_7N_2S.C_{12}H_{23}N$:
C, 64.16; H, 8.23;
N, 6.24; S, 4.76.
Found: C, 63.80; H, 8.28;
N, 6.13; S, 4.70.

EXAMPLE 3

Production of Boc-Lys(Mtr)OH.DCHA

To a mixture 10 ml of dioxane and 5 ml of water was added 1.10 g of Lys(Mtr), followed by addition of 0.63 ml of triethylamine. Then, 0.81 g of Boc-ON was added and the whole mixture was stirred overnight. The dioxane was distilled off and the residue was acidified with aqueous citric acid and extracted with ethyl acetate. The extract was dried over anhydrous sodium sulfate. The solvent was then distilled off and the residue was dissolved in ether. To the solution was added 0.60 ml of DCHA and the crystalline precipitate was collected by filtration.

Yield 1.26 g (65.6%).
m.p. 169°-170° C.
$[\alpha]_D^{22} +8.6°$ (C=0.88, methanol).
$R_f^1$: 0.71.
Elemental analysis:
Calcd. for $C_{21}H_{34}O_7N_2S.C_{12}H_{23}N$:
C, 61.94; H, 8.98;
N, 6.57; S, 5.01.
Found: C, 62.18; H, 9.22;
N, 6.50; S, 5.07.

EXAMPLE 4

Production of Mtr-Gly-OH

In 5 ml of 2 N sodium hydroxide was dissolved 0.75 g of glycine and the solution was ice-cooled. A solution of Mtr-Cl (2.48 g) in THF (10 ml) and 5 ml of 2 N sodium hydroxide were added dropwise and the mixture was stirred for about 3 hours. The reaction mixture was acidified with citric acid and the THF was distilled off. The residue was extracted with ethyl acetate and the extract was washed with water and dried over anhydrous sodium sulfate. The solvent was then distilled off and the crystalline residue was collected by filtration and recrystallized from ethyl acetate.

Yield 0.80 g (27.8%).
m.p. 149°-152° C.
$R_f^1$: 0.49.
Elemental analysis:
Calcd. for $C_{12}H_{17}O_5NS$:
C, 50.16; H, 5.97;
N, 4.88; S, 11.16.
Found: C, 50.21; H, 6.07;
N, 4.78; S, 11.14.

EXAMPLE 5

Production of Mtr-Ile-OH.CHA

In 30 ml of water was suspended 2.16 g of Ile, and 2.80 g of sodium hydrogen carbonate was added. The mixture was heated until dissolution of Ile and then ice-cooled. Thereto was added 20 ml of THF, then a solution of Mtr-Cl (3.73 g) in THF (10 ml) was added, and the mixture was stirred overnight. The THF was distilled off and the residue was acidified with citric acid and extracted with ether. The extract was dried over anhydrous sodium sulfate. The solvent was then distilled off and the residue was dissolved in a small amount of ether. To the solution was added 1.0 ml of CHA and the crystalline precipitate was collected by filtration.

Yield 3.50 g (52.7%).
m.p. 189°-190° C.
$[\alpha]_D^{23} +13.6°$ (C=1.06, methanol).
$R_f^1$: 0.64.
Elemental analysis:
Calcd. for $C_{16}H_{25}O_5NS.C_6H_{13}N$:
C, 59.70; H, 8.65;
N, 6.33; S, 7.25.
Found: C, 59.99; H, 8.41;
N, 6.28; S, 7.09.

EXAMPLE 6

Test for Cleavability of the Amino-Protecting Group Mtr (1) Lys(Mtr)

To 10 mg of Lys(Mtr) was added 1 ml of 0.1 M MSA-TFA-thioanisole (9:1) and the mixture was allowed to stand at room temperature for 1-2 hours. The course of reaction was followed up by TLC; a spot corresponding to Lys appeared upon color reaction with ninhydrin, with complete disappearance of the spot corresponding to Lys(Mtr). Lys(Mtr) was stable against TFA treatment.

(2) Mtr-Gly-OH

To 20 mg of Mtr-Gly-OH was added 0.5 ml of TFA-thioanisole (9:1) and the mixture was allowed to stand at room temperature for 2 hours. The course of reaction was followed up by TLC; a spot corresponding to Gly appeared upon color reaction with ninhydrin, with complete disappearance of the spot corresponding to Mtr-Gly-OH. Mtr-Gly-OH was stable against TFA treatment. The above results revealed that the amino-protecting group Mtr can be eliminated under mild conditions.

EXAMPLE 7

Production of Chicken Gastrin-Releasing Peptide (GRP)

(1) Production of Boc-Leu-Met-NH$_2$

To Boc-Met-NH$_2$ (10.3 g) was added 40 ml of 4 N HCl-acetic acid and the mixture was shaken to give a crystalline precipitate. Ether was added and the above crystalline product was collected by filtration and dried. It was dissolved in 200 ml of DMF, and the solution was ice-cooled. To the solution was added Boc-Leu-ONB (prepared from 8.0 g of Boc-Leu-OH, 6.85 g of HONB and 7.83 g of DCC) together with 7.0 ml of TEA and the mixture was stirred overnight. The solvent was then distilled off and the residue was dissolved in ethyl acetate, washed with aqueous sodium bicarbonate and aqueous citric acid and dried over anhydrous sodium sulfate. The solvent was distilled off to give a crystalline precipitate and, following addition of ether, it was collected by filtration and recrystallized from methanol-ether.

Yield 10.8 g (86.3%).
m.p. 152°-154° C., $[\alpha]_D^{23} -34.2°$ (C=1.03, DMF),
$R_f^1$: 0.65.
Elemental analysis:
Calcd. for $C_{16}H_{31}O_4N_3S$:
C, 53.15; H, 8.64; N, 11.63; S, 8.87.
Found: C, 53.56; H, 8.72; N, 11.47; S, 8.92.

(2) Production of Boc-His(Mtr)OH.DCHA

In a mixture of 30 ml of water and 30 ml of acetone was dissolved 5.11 g of Boc-His-OH and the solution was ice-cooled. To the solution was added 5.6 ml of TEA, then a solution of 4.97 g of Mtr-Cl in 30 ml of acetone was added and the mixture was stirred for 2 hours. The acetone was distilled off under reduced pressure, and the residue was acidified with citric acid, extracted with ethyl acetate, washed with water and dried over anhydrous sodium sulfate. The solvent was then distilled off and the residue was dissolved in a small amount of ethyl acetate. To the solution was added 3.6 ml of DCHA, the solvent was distilled off and the residue was allowed to stand in a refrigerator overnight. Following addition of ether, the crystalline precipitate was collected by filtration.

Yield 7.80 g (60.1%).

m.p. 136°–137° C., $[\alpha]_D^{23} +18.8°$ (C=1.01, methanol).

$R_f^1$: 0.63.

Elemental analysis:

Calcd. for $C_{33}H_{52}O_7N_4S$:

C, 61.08; H, 8.08; N, 8.64; S, 4.94.

Found: C, 61.19; H, 8.05; N, 8.89; S, 4.73.

(3) Production of Boc-His(Mtr)-Leu-MetNH$_2$

To 10.0 g of Boc-Leu-MetNH$_2$ was added 30 ml of 4 N HCl-acetic acid and the mixture was allowed to stand at room temperature for 20 minutes. Ether was added and the precipitate was collected by filtration and dried. Separately, 16.0 g of Boc-His(Mtr)OH.DCHA was suspended in ethyl acetate, followed by addition of 27 ml of 1 N sulfuric acid. The organic layer was taken and dried over anhydrous sodium sulfate. The solvent was then distilled off and the residue was dissolved in 100 ml of acetonitrile. Then, 5.0 g of HONB was added, the mixture was ice-cooled, and 5.8 g of DCC was added. The reaction was allowed to proceed overnight and the precipitate (DCU) was filtered off. The previously obtained amine was dissolved in 100 ml of DMF together with 4.6 ml of TEA. The active ester was added and the mixture was stirred for 6 hours. The solvent was then distilled off, and the residue was dissolved in ethyl acetate, washed with aqueous sodium bicarbonate, aqueous citric acid and water in that order, and dried over anhydrous sodium sulfate. The solvent was distilled off, ether was added, and the mixture was filtered to give a powder.

Yield 15.1 g (86.0%).

m.p. 129°–131° C., $[\alpha]_D^{23} -13.8°$ (C=0.87, DMF). $R_f^1$: 0.64.

Elemental analysis:

Calcd. for $C_{32}H_{50}O_8N_6S_2$:

C, 54.06; H, 7.09; N, 11.82; S, 9.02.

Found: C, 54.69; H, 7.39; N, 11.97; S, 8.39.

(4) Production of Z-Val-Gly-OBu$^t$

Z-Gly-OBu$^t$ (12.0 g) was subjected to catalytic reduction in methanol. The solvent was distilled off and the residue was dissolved in DMF. To the solution were added 8.80 g of Z-Val-OH, 7.20 g of HONB and 8.24 g of DCC under ice-cooling and the mixture was stirred overnight. The precipitate (DCU) was removed by filtration and the residue was dissolved in ethyl acetate, washed with aqueous sodium bicarbonate and aqueous citric acid, and dried over anhydrous sodium sulfate. The solvent was then distilled off and petroleum ether was added to the residue. The resultant crystalline precipitate was collected by filtration and recrystallized from ethyl acetate-petroleum ether.

Yield 11.1 g (87.0%).

m.p. 141° C., $[\alpha]_D^{23} -21.1°$ (C=1.16, DMF), $R_f^1$: 0.80.

Elemental analysis:

Calcd. for $C_{19}H_{28}O_5N_2$:

C, 62.62; H, 7.74; N, 7.69.

Found: C, 62.49; H, 7.60, N, 7.72.

(5) Production of Z-Ala-Val-Gly-OBu$^t$

Z-Val-Gly-OBu$^t$ (10.0 g) was subjected to catalytic reduction in methanol. The reduction product was dissolved in 100 ml of DMF and 5.7 g of Z-Ala-OH and 4.1 g of HONB were added. To the mixture was added 6.2 g of DCC under ice-cooling and the resulting mixture was stirred overnight. The precipitate (DCU) was removed by filtration. The solvent was distilled off to give a crystalline precipitate and, after addition of ethyl acetate, it was collected by filtration and washed well with ethyl acetate.

Yield 10.5 g (96.4%).

m.p. 184°–185° C., $[\alpha]_D^{23} -7.8°$ (C=1.06, DMF).

$R_f^1$: 0.67.

Elemental analysis:

Calcd. for $C_{22}H_{33}O_6N_3$:

C, 60.67; H, 7.64; N, 9.65.

Found: C, 60.93; H, 7.86; N, 9.77.

(6) Production of Z-Trp(Mtr)-Ala-Val-Gly-OBu$^t$

Z-Ala-Val-Gly-OBu$^t$ (5.0 g) was subjected to catalytic reduction in methanol. The solvent was distilled off and the residue was dissolved in 100 ml of DMF. To the solution were added 6.34 g of Z-Trp(Mtr)OH and 1.86 g of HOBT and the mixture was ice-cooled. Then, 2.85 g of DCC was added and the whole mixture was stirred overnight. The precipitate (DCU) was removed by filtration and the solvent was distilled off. The residue was extracted with ethyl acetate containing a small amount of n-butanol. The extract was washed with aqueous sodium bicarbonate and dried over anhydrous sodium sulfate. The solvent was then distilled off and ether was added to the residue. The precipitate was collected by filtration and crystallized from methanol-ethyl acetate-ether.

Yield 8.80 g (96.6%).

m.p. 154°–155° C., $[\alpha]_D^{23} -22.7°$ (C=0.88, DMF).

$R_f^1$: 0.68.

Elemental analysis:

Calcd. for $C_{44}H_{56}O_{10}N_5S$:

C, 61.85; H, 6.76; N, 8.39; S, 3.84.

Found: C, 62.06; H, 7.01; N, 8.58; S, 3.58.

(7) Production of Boc-His(Mtr)-Trp(Mtr)-Ala-Val-Gly-OBu$^t$

Z-Trp(Mtr)-Ala-Val-Gly-OBu$^t$ (8.0 g) was subjected to catalytic reduction in DMF-methanol and the methanol was distilled off. Boc-His(Mtr)OH [prepared from 6.22 g of Boc-His(Mtr)OH.DCHA] and 1.90 g of HONB were added and the mixture was ice-cooled. Then, 2.18 g of DCC was added and the whole mixture was stirred overnight. The DCU precipitate was removed by filtration and the solvent was distilled off. Ether was added and the precipitate was collected by filtration and washed with a methanol-ethyl acetate-ether mixture.

Yield 10.2 g (92.5%).

m.p. 202°–204° C., $[\alpha]_D^{23} -16.1°$ (C=1.18, DMF).

$R_f^1$: 0.68.

Elemental analysis:

Calcd. for $C_{56}H_{77}O_{14}N_8S_2$:

C, 58.46; H, 6.75; N, 9.74; S, 5.57.

Found: C, 58.32; H, 6.54; N, 9.58; S, 5.51.

(8) Production of Boc-Ser-His(Mtr)-Trp(Mtr)-Ala-Val-Gly-OH

To 4.0 g of Boc-His(Mtr)-Trp(Mtr)-Ala-Val-Gly-OBu$^t$ was added 30 ml of TFA and the mixture was shaken at room temperature for 50 minutes. The TFA was distilled off and ether was added. The precipitate was collected by filtration and dried. Separately, 0.76 g of Boc-Ser-OH and 0.72 of HONB were dissolved in 20 ml of acetonitrile and the solution was ice-cooled. Then, 0.83 g of DCC was added and the mixture was stirred for 4 hours. The previously prepared amine was dissolved in 50 ml of DMF together with 1.0 ml of TEA. The active ester was added and the mixture was stirred overnight. The solvent was then distilled off and a small amount of acetic acid and then water were added. The precipitate was collected by filtration and reprecipitated from DMF-water.

Yield 3.60 g (85.0%).
m.p. 148°–152° C., $[\alpha]_D^{23}$ −16.4° (C=1.09, DMF).
Elemental analysis:
Calcd. for $C_{55}H_{74}O_{16}N_9S_22H_2O$:
C, 54.26; H, 6.46; N, 10.36; S, 5.27.
Found: C, 54.58; H, 6.33; N, 10.82; S, 5.51.

(9) Production of Z-Arg(Pme)-Gly-OBu$^t$

Z-Gly-OBu$^t$ (13 g) was subjected to catalytic reduction in methanol. The solvent was distilled off and the residue was dissolved in 200 ml of DMF. To the solution was added Z-Arg(Pme)OH [prepared from 20 g of Z-Arg(Pme)OH.CHA] and the mixture was ice-cooled. Then, 5.4 g of HOBT and 8.2 g of DCC were added and the whole mixture was stirred overnight. The precipitate (DCU) was removed by filtration and the solvent was distilled off. The residue was dissolved in ethyl acetate, washed with aqueous sodium bicarbonate and aqueous citric acid and dried over anhydrous sodium sulfate. The solvent was distilled off, petroleum ether was added and the mixture was filtered to give a powder.

Yield 19.8 g (95.0%).
m.p. 55°–60° C., $[\alpha]_D^{23}$ +0.2° (C=0.88, DMF), $R_f^1$: 0.62.
Elemental analysis:
Calcd. for $C_{31}H_{45}O_7N_5S$:
C, 58.93; H, 7.18; N, 11.09; S, 5.08.
Found: C, 58.96; H, 7.01; N, 10.67; S, 5.05.

(10) Production of Z-Tyr-Pro-OBu$^t$

Z-Pro-OBu$^t$ (15.0 g) was subjected to catalytic reduction in 300 ml methanol. The solvent was distilled off and the residue was dissolved in 400 ml of DMF. To the solution was added Z-Tyr-OH (prepared from 20.0 g of Z-Tyr-OH.DCHA) followed by addition of 6.75 g of HOBT. To the ice-cooled mixture was added 10.4 g of DCC and the whole mixture was stirred overnight. The precipitate (DCU) was removed by filtration and the solvent was distilled off. The residue was dissolved in ethyl acetate, washed with aqueous sodium bicarbonate and aqueous citric acid and dried over anhydrous sodium sulfate. The solvent was then distilled off and the residue was chromatographed on a silica gel column (7.5×9 cm) using 1% MeOH-chloroform as an eluant. The active fractions are combined and concentrated. To the residue was added petroleum ether and the mixture was filtered to give a powder.

Yield 15.4 g (82.2%).
$[\alpha]_D^{23}$ −39.9° (C=0.83, DMF), $R_f^1$: 0.62.
Elemental analysis:
Calcd. for $C_{26}H_{32}O_6N_2 \cdot \frac{1}{2}H_2O$:
C, 65.39; H, 6.97; N, 5.87.
Found: C, 65.70; H, 6.93; N, 5.66.

(11) Production of Z-Ile-Tyr-Pro-OBu$^t$

Z-Tyr-Pro-OBu$^t$ (15.2 g) was dissolved in 300 ml of methanol and subjected to catalytic reduction. The solvent was distilled off and the residue was dissolved in 200 ml of DMF. To the solution were added 8.0 g of Z-IleOH and 6.5 g of HONB and the mixture was ice-cooled. Then, 7.4 g of DCC was added and the whole mixture was stirred overnight. A small amount of N,N-dimethyl-1,3-propane-diamine was added, the DCU was removed by filtration and the solvent was distilled off under reduced pressure. The residue was dissolved in ethyl acetate, washed with aqueous sodium bicarbonate and aqueous citric acid and dried over anhydrous sodium sulfate. The solvent was then distilled off to give a crystalline precipitate and, following addition of petroleum ether, it was collected by filtration and recrystallized from methanol-ether-petroleum ether.

Yield 10.9 g (62.5%).
m.p. 177°–178° C., $[\alpha]_D^{23}$ −38.3° (C=1.11, DMF).
$R_f^1$: 0.62.
Elemental analysis:
Calcd. for $C_{32}H_{43}O_7N_3$:
C, 66.07; H, 7.45; N, 7.22.
Found: C, 66.07; H, 7.74; N, 7.19.

(12) Production of Z-Ile-Tyr-Pro-OH

To 6.0 g of Z-Ile-Tyr-Pro-OBu$^t$ was added 60 ml of TFA and the mixture was stirred at room temperature for an hour and concentrated. The residue was dissolved in ethyl acetate, washed with water and dried over anhydrous sodium sulfate. The solvent was then distilled off, ether was added and the mixture was filtered to give a powder.

Yield 5.10 g (94.2%).
M.P. 72°–74° C., $[\alpha]_D^{23}$ −25.2° (C=1.01, DMF).
$R_f^1$: 0.44.
Elemental analysis:
Calcd. for $C_{28}H_{35}O_7N_3$:
C, 63.98; H, 6.71; N, 7.99.
Found: C, 63.75; H, 6.67; N, 7.84.

(13) Production of Z-Ile-Tyr-Pro-Arg(Pme)-Gly-OBu$^t$

Z-Arg(Pme)-Gly-OBu$^t$ (7.58 g) was dissolved in 300 ml of methanol and, following addition of 12 ml of 1 N hydrochloric acid, it was subjected to catalytic reduction. The solvent was distilled off and the residue was dissolved in 100 ml of DMF together with 20.0 ml of TEA. To this solution were added 5.78 g of Z-Ile-Tyr-Pro-OH, 2.23 g of HOBT and 3.40 g of DCC and the mixture was stirred overnight. The precipitate (DCU) was removed by filtration, the solvent was distilled off, and the residue was dissolved in ethyl acetate. The solution was washed with aqueous sodium bicarbonate and aqueous citric acid and dried over anhydrous sodium sulfate. The solvent was then distilled off and the residue was chromatographed on a silica gel column (5.5×10 cm) using 2% MeOH-chloroform as an eluant. The fractions containing the desired product were combined and concentrated. To the residue was added ether and the mixture was filtered to give a powder.

Yield 7.20 g (62.2%).
M.P. 110°–112° C., $[\alpha]_D^{23}$ −28.3° (C=1.19, DMF).
$R_f^1$: 0.59.
Elemental analysis:
Calcd. for $C_{51}H_{72}O_{11}N_8S \cdot H_2O$:
C, 59.85; H, 7.29; N, 10.93; S, 3.13.
Found: C, 60.16; H, 7.56; N, 10.95; S, 2.98.

(14) Production of Z-Lys(Mtr)-Ile-Tyr-Pro-Arg(Pme)-Gly-OBu$^t$

Z-Ile-Tyr-Pro-Arg(Pme)-Gly-OBu$^t$ (7.0 g) was dissolved in 350 ml of methanol and, following addition of 7 ml of 1 N hydrochloric acid, it was subjected to catalytic reduction. The solvent was distilled off and the residue was dissolved in 200 ml of DMF together with 1.0 ml of TEA. To this solution were added Z-Lys(Mtr)-OH [prepared from 4.74 g of Z-Lys(Mtr)OH.DCHA], 1.20 g of HOBT and 1.80 g of DCC and the mixture was stirred overnight. The precipitate (DCU) was removed by filtration, the solvent was distilled off, and the residue was dissolved in ethyl acetate. The solution was washed with aqueous sodium bicarbonate and aqueous citric acid and dried over anhydrous sodium sulfate. The solvent was then distilled off and ether was added to give a powder, which was reprecipitated twice with ethyl acetate-ether.

Yield 8.40 g (87.5%).

m.p. 116°–118° C., $[\alpha]_D^{23}$ −19.9° (C=1.05, DMF).

$R_f^1$: 0.59.

Elemental analysis:

Calcd. for $C_{66}H_{96}O_{15}N_{10}S_2$:

C, 59.44; H, 7.26; N, 10.50; S, 4.81.

Found: C, 59.10; H, 7.44; N, 10.46; S, 4.98.

(15) Production of Z-Thr-Lys(Mtr)-Ile-Tyr-Pro-Arg(Pme)-Gly-OBu$^t$

Z-Lys(Mtr)-Ile-Tyr-Pro-Arg(Pme)-Gly-OBu$^t$ (7.50 g) was subjected to catalytic reduction in 350 ml of methanol. The solvent was distilled off and the residue was dissolved in 100 ml of DMF. To the solution were added 1.49 g of Z-Thr-OH, 1.51 g of HONB and 1.73 g of DCC and the mixture was stirred overnight. A small amount of N,N-dimethyl -1,3-propanediamine was added, the precipitate (DCU) was filtered off and the solvent was distilled off. The residue was dissolved in ethyl acetate containing a small amount of n-butanol and the solution was washed with aqueous sodium bicarbonate and dried over anhydrous sodium sulfate. The solvent was then distilled off and ether was added to the residue to give a powder, which was collected by filtration.

Yield 8.0 g (99.2%).

m.p. 122°–124° C. $[\alpha]_D^{23}$ −25.5° (C=0.82, DMF).

$R_f^1$: 0.59.

Elemental analysis:

Calcd. for $C_{70}H_{103}O_{17}N_{11}S_2$:

C, 58.60; H, 7.24; N, 10.74; S, 4.47.

Found: C, 58.61; H, 7.29; N, 10.47; S, 4.02.

(16) Production of Boc-Leu-Thr-Lys(Mtr)-Ile-Tyr-Pro-Arg(Pme)-Gly-OBu$^t$

Z-Thr-Lys(Mtr)-Ile-Tyr-Pro-Arg(Pme)-Gly-OBu$^t$ (7.5 g) was dissolved in methanol and, following addition of 0.99 g of p-toluenesulfonic acid, it was subjected to catalytic reduction. The solvent was distilled off and the residue was dissolved in 100 ml of DMF together with 0.74 ml of TEA. The solution was ice-cooled. To this solution were added 1.37 g of Boc-Leu-OH, 1.41 g of HONB and 1.62 g of DCC and the mixture was stirred overnight. The DCU was filtered off and the solvent was distilled off. The residue was dissolved in ethyl acetate, washed with aqueous sodium bicarbonate and aqueous citric acid and dried over anhydrous sodium sulfate. The solvent was then distilled off, ether was added, and the mixture was filtered to give a powder.

Yield 7.55 g (95.4%).

m.p. 136°–138° C., $[\alpha]_D^{23}$ −26.6° (C=1.00, DMF).

$R_f^1$: 0.59.

Elemental analysis:

Calcd. for $C_{73}H_{116}O_{18}N_{12}S_2\cdot H_2O$:

C, 57.23; H, 7.76; N, 10.97; S, 4.19.

Found: C, 57.53; H, 8.12; N, 10.65; S, 3.90.

(17) Production of Boc-Ala-Leu-Thr-Lys(Mtr)-Ile-Tyr-Pro-Arg(Pme)-Gly-OH

To 4.20 g of Boc-Leu-Thr-Lys(Mtr)-Ile-Tyr-Pro-Arg(Pme)-Gly-OBu$^t$ was added 40 ml of TFA and the mixture was shaken at room temperature for 60 minutes. The solvent was distilled off and ether was added. The mixture was filtered to give a powder. It was dried and dissolved in 50 ml of DMF. The solution was ice-cooled and 0.80 ml of TEA was added. Then, Boc-Ala-ONB [prepared from 0.52 g of Boc-Ala-OH, 0.54 g of HONB and 0.62 g of DCC] was added and the whole mixture was stirred overnight. A small amount of N,N-dimethyl-1,3-propanediamine was added and the solvent was then distilled off and aqueous acetic acid was added. The precipitate was collected by filtration ahd reprecipitated from aqueous methanol.

Yield 3.60 g (88.1%).

m.p. 128°–130° C., $[\alpha]_D^{23}$ −32.9° (C=0.98, DMF).

$R_f^1$: 0.40.

Elemental analysis:

Calcd. for $C_{72}H_{113}O_{19}N_{13}S_2\cdot 2H_2O$:

C, 55.26; H, 7.54; N, 11.64; S, 4.10.

Found: C, 55.02; H, 6.80; N, 11.38; S, 3.77.

(18) Production of Z-Ser-Pro-OBu$^t$

Z-Pro-OBu$^t$ (11.0 g) was dissolved in 300 ml of methanol and subjected to catalytic reduction. The solvent was distilled off and the residue was dissolved in 200 ml of DMF. Then, 7.2 g of Z-Ser-OH, 4.90 g of HOBT and 7.50 g of DCC were added and the mixture was stirred overnight. The precipitate (DCU) was filtered off and the solvent was distilled off. The residue was dissolved in ethyl acetate, washed with aqueous sodium bicarbonate and dried over anhydrous sodium sulfate. The solvent was then distilled off and ether was added. The crystalline precipitate was collected by filtration and recrystallized from ethyl acetate-ether.

Yield 9.50 g (67.2%).

m.p. 126°–127° C., $[\alpha]_D^{23}$ −50.0° (C=0.95, DMF).

$R_f^1$: 0.65.

Elemental analysis:

Calcd. for $C_{20}H_{28}O_6N_2$:

C, 61.21; H, 7.19; N, 7.14.

Found: C, 61.45; H, 7.16; N, 7.31.

(19) Production of Z-Gly-Ser-Pro-OBu$^t$

Z-Ser-Pro-OBu$^t$ (10.0 g) was dissolved in 300 ml of methanol and subjected to catalytic reduction. The solvent was distilled off and the residue was dissolved in 300 ml of DMF. Then, 5.06 g of Z-Gly-OH and 5.13 g of HONB were added and the mixture was ice-cooled. To the mixture was added 5.89 g of DCC and the whole mixture was stirred overnight. A small amount of N,N-dimethyl-1,3-propanediamine was added and the DCU was filtered off. The solvent was then distilled off and the residue was dissolved in ethyl acetate, washed with aqueous sodium bicarbonate and aqueous citric acid and dried over anhydrous sodium sulfate. The solvent was distilled off and petroleum ether was added. The crystalline precipitate was collected by filtration and recrystallized from ether.

Yield 7.70 g (72.1%).

m.p. 96°–98° C., $[\alpha]_D^{23}$ −53.4° (C=1.05, DMF).

$R_f^1$: 0.61.

Elemental analysis:

Calcd. for $C_{22}H_{31}O_7N_3$:
C, 58.78; H, 6.95; N, 9.35.
Found: C, 58.86; H, 7.04; N, 9.46.

(20) Production of Z-Gly-Gly-Ser-Pro-OBu$^t$

Z-Gly-Ser-Pro-OBu$^t$ (7.0 g) was dissolved in 200 ml of methanol and subjected to catalytic reduction. The solvent was distilled off and the residue was dissolved in 100 ml of DMF. To the solution were added 3.0 g of Z-Gly-OH and 3.10 g of HONB and the mixture was ice-cooled. Then, 3.60 g of DCC was added and the whole mixture was stirred overnight. A small amount of N,N-dimethyl-1,3-propanediamine was added and the DCU was filtered off. The solvent was then distilled off and the residue was dissolved in ethyl acetate, washed with saturated aqueous sodium chloride and dried over anhydrous sodium sulfate. The solvent was distilled off and petroleum ether was added. The crystalline precipitate was collected by filtration and recrystallized from ether.

Yield 5.70 g (78.5%).
m.p. 129°-130° C., $[\alpha]_D^{23} - 47.0°$ (C=0.81, DMF).
$R_f^1$: 0.47.
Elemental analysis:
Calcd. for $C_{24}H_{34}O_8N_4$:
C, 56.90; H, 6.77; N, 11.06.
Found: C, 56.75; H, 6.68; N, 10.90.

(21) Production of Z-Gln-Pro-OBu$^t$

Z-Pro-OBu$^t$ (16.2 g) was dissolved in 350 ml of methanol and subjected to catalytic reduction. The solvent was distilled off and the residue was dissolved in 200 ml of DMF. To this solution were added 12.4 g of Z-Gln-OH and 7.16 g of HOBT and the mixture was ice-cooled. Then, 10.9 g of DCC was added and the whole mixture was stirred overnight. The precipitate (DCU) was filtered off and the solvent was distilled off. The residue was dissolved in ethyl acetate, washed with aqueous sodium bicarbonate and aqueous citric acid and dried over anhydrous sodium sulfate. The solvent was then distilled off and petroleum ether was added. The crystalline precipitate was collected by filtration and recrystallized from ethyl acetatepetroleum ether.

Yield 15.8 g (82.5%).
m.p. 106°-107° C., $[\alpha]_D^{23} - 51.2°$ (C=1.06, DMF).
$R_f^1$: 0.62.
Elemental analysis:
Calcd. for $C_{22}H_{31}O_6N_3$:
C, 60.95; H, 7.21; N, 9.69.
Found: C, 60.95; H, 7.36; N, 9.41.

(22) Production of Z-Leu-Gln-Pro-OBu$^t$

In 300 ml of methanol were dissolved 8.0 g of Z-Gln-Pro-OBu$^t$ and 3.51 g of p-toluenesulfonic acid and catalytic reduction was carried out. The solvent was then distilled off and the residue was dissolved in 200 ml of DMF together with 2.6 ml of TEA. The solution was ice-cooled. To this solution were added Z-Leu-OH [prepared from 8.24 g of Z-Leu-OH.DCHA], 4.00 g of HONB and 4.60 g of DCC and the mixture was stirred overnight. A small amount of N,N-dimethyl-1,3-propanediamine was added and the DCU was removed by filtration. The solvent was distilled off and the residue was dissolved in ethyl acetate, washed with aqueous sodium bicarbonate and aqueous citric acid and dried over anhydrous sodium sulfate. The solvent was distilled off and, following addition of petroleum ether, the crystalline precipitate was collected by filtration and recrystallized from ethyl acetate-petroleum ether.

Yield 7.70 g (76.3%).
m.p. 62°-64° C., $[\alpha]_D^{23} - 51.7°$ (C=1.11, DMF).
$R_f^1$: 0.61.
Elemental analysis:
Calcd. for $C_{28}H_{42}O_7N_4$:
C, 61.52; H, 7.75; N, 10.25.
Found: C, 61.19; H, 7.75; N, 10.11.

(23) Production of Boc-Pro-Leu-Gln-Pro-OBu$^t$

Z-Leu-Gln-Pro-OBu$^t$ (7.0 g) was dissolved in 300 ml of methanol and subjected to catalytic reduction. The solvent was distilled off and the residue was dissolved in 100 ml of DMF. To the solution were added 2.42 g of Boc-Pro-OH and 2.76 g of HONB and the mixture was ice-cooled. Then, 3.17 g of DCC was added and the mixture was stirred overnight. A small amount of N,N-dimethyl-1,3-propanediamine was added and the DCU was removed by filtration. The solvent was distilled off and the residue was dissolved in ethyl acetate. The solution was washed with aqueous sodium bicarbonate and aqueous citric acid and dried over anhydrous sodium sulfate. The solvent was distilled off and ether-petroleum ether was added. The mixture was filtered to give a powder.

Yield 6.50 g (83.3%).
m.p. 74°-76° C., $[\alpha]_D^{23} - 76.3°$ (C=1.19, DMF).
$R_f^1$: 0.60.
Elemental analysis:
Calcd. for $C_{30}H_{51}O_8N_5$:
C, 59.05; H, 8.43; N, 11.49.
Found: C, 58.89; H, 8.12; N, 11.08.

(24) Production of Boc-Ala-Pro-Leu-Gln-Pro-OH

To 6.0 g of Boc-Pro-Leu-Gln-Pro-OBu$^t$ was added 60 ml of TFA and the mixture was stirred at room temperature for 60 minutes. The solvent was distilled off and ether was added to the residue. The mixture was filtered to give a powder. This powdery product was dried and dissolved in 100 ml of DMF. The solution was ice-cooled and 2.80 ml of TEA was added. To the solution were added Boc-Ala-ONB [prepared from 1.95 g of Boc-Ala-OH, 2.07 g of HONB and 2.38 g of DCC] and the mixture was stirred overnight. The solvent was then distilled off and a small amount of acetic acid was added. Then, ether was added and the mixture was filtered to give a powdery product. This product was dissolved in chloroform and chromatographed on a silica gel column (5.5×8 cm) using 5% methanol-chloroform as an eluant. The fractions containing the desired product are collected and concentrated. Ether was added and the mixture was filtered to give a powder.

Yield 4.50 g (73.2%).
m.p. 124°-128° C., $[\alpha]_D^{23} - 82.1°$ (C=1.04, DMF).
$R_f^1$: 0.18.
Elemental analysis:
Calcd. for $C_{29}H_{43}O_9N_6$:
C, 55.75; H, 7.74; N, 13.45.
Found: C, 55.38; H, 7.65; N, 13.21.

(25) Production of Boc-Ala-Pro-Leu-Gln-Pro-Gly-Gly-Ser-Pro-OBu$^t$

Z-Gly-Gly-Ser-Pro-OBu$^t$ (2.23 g) was dissolved in 100 ml of methanol and subjected to catalytic reduction. The solvent was distilled off and the residue was dissolved in 50 ml of DMF. To the solution were added 2.50 g of Boc-Ala-Pro-Leu-Gln-Pro-OH and 0.90 g of HONB and the mixture was ice-cooled. Then, 1.03 g of DCC was added and the mixture was stirred overnight. The precipitate (DCU) was removed by filtration and the solvent was dissolved off. The residue was dissolved inethyl acetate containing a small amount of n-BuOH and the solution was washed with saturated aqueous sodium chloride and dried over anhydrous sodium sulfate. The solvent was distilled off and ether was added. The mixture was filtered to give a powder.

Yield 3.85 g (98.3%).
m.p. 100°–105° C., $[\alpha]_D^{23} -74.0°$ (C=0.92, DMF). $R_f^1$: 0.19.
Elemental analysis:
Calcd. for $C_{45}H_{74}O_{14}N_{10}·H_2O$:
C, 54.20; H, 7.68; N, 14.05.
Found: C, 54.01; H, 7.45; N, 13.44.

(26) Production of Boc-Ala-Pro-Leu-Gln-Pro-Gly-Gly-Ser-Pro-OH

To 1.0 g of Boc-Ala-Pro-Leu-Gln-Pro-Gly-Gly-Ser-Pro-OBu$^t$ was added 10 ml of TFA and the mixture was shaken at room temperature for an hour. The solvent was distilled off and ether was added. The mixture was filtered to give a powdery product. This product was dissolved in 10 ml of DMF and the solution was ice-cooled. To the solution were added 0.46 ml of TEA and then 0.27 g of Boc-ON and the mixture was stirred for 4 hours. The solvent was distilled off and 1.5 ml of ethyl acetate was added. Then, ether was added and the mixture was filtered to give a powder, which was reprecipitated from methanol-ether.

Yield 0.87 g (92.4%).
m.p. 141°–145° C., $[\alpha]_D^{23} -72.9°$ (C=0.98, DMF). $R_f^3$: 0.29.
Elemental analysis:
Calcd. for $C_{41}H_{66}O_{14}N_{10}.3H_2O$:
C, 50.40; H, 7.43; N, 14.34.
Found: C, 50.16; H, 6.76; N, 14.11.

(27) Production of Boc-Ser-His(Mtr)-Trp(Mtr)-Ala-Val-Gly-His(Mtr)-Leu-Met-NH$_2$ To 3.97 g of Boc-His(Mtr)-Leu-MetNH$_2$ was added 40 ml of TFA and the mixture was shaken at room temperature for 10 minutes. Then, 4.1 ml of 1.3 N hydrochloric acid was added, the solvent was distilled off, and ether was added. The mixture was filtered to give a powdery product. This product was dried and dissolved in 40 ml of DMF and the solution was ice-cooled. To this solution were added 0.86 ml of TEA and then 5.50 g of Boc-Ser-His(Mtr)-Trp(Mtr)-Ala-Val-Gly-OH, 1.0 g of HONB and 1.15 g of DCC and the whole mixture was stirred overnight. The precipitate (DCU) was removed by filtration and the solvent was distilled off. Water was added and the mixture was filtered to give a powder, which was washed with aqueous ethanol.

Yield 7.35 g (88.9%).
m.p. 192°–193° C., $[\alpha]_D^{23} -12.5°$ (C=1.05, DMF). $R_f^1$: 0.50.
Elemental analysis:
Calcd. for $C_{82}H_{114}O_{21}N_{15}S_4$:
C, 55.51; H, 6.48; N, 11.84; S, 7.23.
Found: C, 55.56; H, 6.74; N, 11.83; S, 6.55.

(28) Production of Boc-Ser-His-Trp(Mtr)-Ala-Val-Gly-His-Leu-Met-NH$_2$

In 15 ml of DMF was dissolved 3.0 g of Boc-Ser-His(Mtr)-Trp(Mtr)-Ala-Val-Gly-His(Mtr)-Leu-Met-NH2 and 2.30 g of HOBT was added. After 30 minutes, the solvent was distilled off and ether was added. The mixture was filtered to give a powder.

Yield 2.15 g (92.5%).
m.p. 191°–193° C., $[\alpha]_D^{23} -18.8°$ (C=0.94, DMF). $R_f^3$: 0.64.
Elemental analysis:
Calcd. for $C_{62}H_{90}O_{15}S_2·H_2O$:
C, 54.45; H, 6.78; N, 15.36; S, 4.69.
Found: C, 53.92; H, 6.43; N, 15.80; S, 4.34.

(29) Production of Boc-Ala-Leu-Thr-Lys(Mtr)-Ile-Tyr-Pro-Arg(Pme)-Gly-Ser-His-Trp(Mtr)-Ala-Val-Gly-His-Leu-Met-NH$_2$ To 2.0 g of Boc-Ser-His-Trp(Mtr)-Ala-Val-Gly-His-Leu-MetNH$_2$ was added 20 ml of TFA and the mixture was allowed to stand at room temperature for 15 minutes. The TFA was distilled off and ether was added. The mixture was filtered to give a powdery product, which was dried and dissolved in 5 ml of DMF. Then, 1.24 ml of TEA was added and the mixture was stirred well. Ether was added and the resultant precipitate was collected by filtration. This powdery product was dissolved in 20 ml of DMF and 1.78 g of Boc-Ala-Leu-Thr-Lys(Mtr)-Ile-Tyr-Pro-Arg(Pme)-Gly-OH and 0.41 g of HONB were added. To the ice-cooled mixture was added 0.47 g of DCC and the whole mixture was stirred overnight. The solvent was then distilled off and ethanol-ethyl acetate was added. The mixture was filtered to give a powder, which was washed with hot ethanol.

Yield 3.30 g (99.7%).
m.p. 222°–223° C. (decompn.), $[\alpha]_D^{23} -22.8°$ (C=1.02, DMF), $R_f^3$: 0.67.
Elemental analysis:
Calcd. for $C_{129}H_{193}O_{31}N_{28}S_4.8H_2O$:
C, 53.34; H, 7.25; N, 13.50; S, 4.42.
Found: C, 53.35; H, 6.98; N, 12.91; S, 4.58.

(30) Production of Boc-Ala-Pro-Leu-Gln-Pro-Gly-Gly-Ser-Pro-Ala-Leu-Thr-Lys(Mtr)-Ile-Tyr-Pro-Arg(Pme)-Gly-Ser-His-Trp(Mtr)-Ala-Val-Gly-His-Leu-Met-NH$_2$ To 500 mg of Boc-Ala-Leu-Thr-Lys(Mtr)-Ile-Tyr-Pro-Arg(Pme)-Gly-Ser-His-Trp(Mtr)-Ala-Val-Gly-His-Leu-Met-NH$_2$ was added 5 ml of TFA and the mixture was shaken. The TFA was distilled off, ether was added. The resulting powdery product was collected by filtration and dissolved in 1 ml of DMF. Then 0.2 ml of TEA was added and the mixture was stirred well. Ether was added and the mixture was filtered. The powdery product was dissolved in 5 ml of DMF and 217 mg of BOC-Ala-Pro-Leu-Gln-Pro-Gly-Gly-Ser-Pro-OH and 50 mg of HOBT were added. The mixture was ice-cooled and thereto was added 160 mg of DCC and the whole mixture was stirred overnight. The precipitate (DCU) was filtered off and the solvent was distilled off. To the residue was added ethyl acetate and the mixture was filtered. The powdery product was dissolved in DMF-methanol and the solution was heated for about 30 minutes. The methanol was distilled off and ether was added to the residue. The mixture was filtered and the resulting powdery product was washed with aqueous methanol.

Yield 480 mg (72.2%).
m.p. 203°–208° C. (decompn.), $[\alpha]_D^{23} -35.2°$ (C=0.93, DMF), $R_f^3$: 0.66.
Elemental analysis:
Calcd. for $C_{165}H_{249}O_{42}N_{38}S_4.6H_2O$:
C, 53.95; H, 7.16; N, 14.49; S, 3.49.
Found: C, 54.08; H, 6.87; N, 14.19; S, 3.43.

(31) Production of H-Ala-Pro-Leu-Gln-Pro-Gly-Gly-Ser-Pro-Ala-Leu-Thr-Lys-Ile-Tyr-Pro-Arg-Gly-Ser-His-Trp-Ala-Val-Gly-His-Leu-Met-NH$_2$ (chicken GRP)

To 100 mg of Boc-Ala-Pro-Leu-Gln-Pro-Gly-Gly-Ser-Pro-Ala-Leu-Thr-Lys(Mtr)-Ile-Tyr-Pro-

Arg(Pme)-Gly-Ser-His-Trp(Mtr)-Ala-Val-Gly-His-Leu-Met NH₂ was added 8 ml of 0.3 M methanesulfonic acid-TFA-thioanisole (9:1) and the mixture was shaken at room temperature for 2 hours. Then, 100 mg of ammonium acetate was added and the TFA was distilled off. Ether was added and the mixture was filtered. The powdery product was dissolved in a small amount of 1 N acetic acid and chromatographed on a Sephadex G-25 column (2.2×120 cm) using 1 N acetic acid as an eluant. The fractions 170 ml-270 ml were collected, lyophilized and dissolved in a small amount of water. The solution was passed through an Amberlite IRA 410 column (1×10 cm) and then chromatographed on a carboxymethylcellulose column (2.2×17 cm). Following elution with water (400 ml)-0.4 M ammonium acetate (400 ml) by the linear gradient method, the fractions 335 ml-365 ml were collected and lyophilized.

Yield 28 mg (35%).

$[\alpha]_D^{23} -102.2°$ (C=0.32, 1% AeOH), $R_f^4$: 0.39.

Amino acid analysis (hydrolysis with 4% thioglycolic acid/6N hydrochloric acid): Lys 1.00(1); His 1.73(2); Arg 1.04(1); Trp 0.67(1); Thr 1.06(1); Ser 1.77(2); Glu 1.11(1); Pro 4.20(4); Gly 4.23(4); Ala 3.19(3); Val 1.06(1); Met 1.02(1); Ile 0.96(1); Leu 3.04(3); Tyr 1.00(1) (Average recovery 73.7%).

EXAMPLE 8

Production of Mastoparan X (1) Production of Z-Leu-Leu-NH₂[Ia]

Z-Leu-NH₂ (5.29 g) was hydrogenated in MeOH (200 ml) and the free base obtained was coupled with Z-Leu-ONB (8.53 g) in DMF (80 ml). After the usual work-up, the product was crystallized from AcOEt-pet. ether: yield 6.82 g (90.3%), mp 201°-202° C., $[\alpha]_D^{23} -17.3°$ (c=0.3 in DMF), $R_f^5$ 0.19.

Elemental analysis Calcd. for C₂₀H₃₁N₃O₄: C, 63.63; H, 8.28; N, 11.13. Found: C, 63.90; H, 8.68; N, 11.29.

(2) Production of Z-Lys(Mtr)-Leu-Leu-NH₂[Ib]

Compound Ia (3.78 g) was hydrogenated in MeOH (200 ml) and the free base was dissolved in DMF (60 ml). To this, Z-Lys(Mtr)-OH (prepared from the DCHA salt (6.6 g)), HONB (2.0 g) and DCC (2.2 g) were added under ice-cooling. The mixture was stirred for 10 h and worked up as usual. The product was crystallized from AcOEt to give needles: yield 5.4 g (75.2%), mp 158°-159° C., $[\alpha]_D^{23} -38.4°$ (c=0.3 in MeOH), $R_f^5$ 0.23.

Elemental analysis Calcd. for C₃₆H₅₅N₅O₈S: C, 60.23; H, 7.72; N, 9.96; S, 4.97. Found: C, 60.33; H, 7.57; N, 9.82; S, 4.28.

(3) Production of Z-Lys(Mtr)-Lys(Mtr)-Leu-Leu-NH₂[Ic]

Compounb Ib (3.59 g) was hydrogenated in MeOH (100 ml) and the free base was dissolved in DMF (50 ml). To this, Z-Lys(Mtr)-OH (prepared from the DCHA salt (3.3 g)), HONB (1.0 g) and DCC (1.2 g) was added under ice-cooling. The mixture was stirred for 10 h and worked up as usual. The product was crystallized from MeOH-AcOEt to give needles: yield 4.7 g (88.8%), mp 222° C., $[\alpha]_D^{23} 25.6°$ (c=0.4 in MeOH), $R_f^5$ 0.08.

Elemental analysis Calcd. for C₅₂H₇₉N₇O₁₂S₂: C, 59.01; H, 7.52; N, 9.27; S, 6.06. Found: C, 59.29; H, 7.72; N, 9.28; S, 6.08.

(4) Production of Z-Ala-Lys(Mtr)-Lys(Mtr)-Leu-Leu-NH₂[Id]

Compound Ic (4.23 g) was hydrogenated in MeOH (100 ml) and the free base was coupled with Z-Ala-ONB (1.54 g) in DMF (50 ml) for 10 h. The solution was concentrated and the resulting residue was triturated with AcOEt to give a precipitate, which was reprecipitated from MeOH-AcOEt: yield 4.2 g (92.9%), mp 206°-209° C., $[\alpha]_D^{23} -28.7°$ (c=0.6 in MeOH), $R_f^5$ 0.11.

Elemental analysis calcd. for C₅₅H₈₄N₈O₁₃S₂: C, 58.49; H, 7.50; N, 9.92; S, 5.68. Found: C, 58.59; H, 7.56; N, 9.83; S, 5.80.

(5) Production of Boc-Met-Ala-Lys(Mtr)-Lys(Mtr)-Leu-Leu-NH₂[Ie]

Compound Id (2.83 g) was hydrogenated in MeOH (100 ml) and the free base was coupled with Boc-Met-ONB (1.03 g) in DMF (20 ml) for 6 h. The solution was concentrated and the residue was triturated with MeOH-ether to give a precipitate, which was reprecipitated from aq. MeOH: yield 3.08 g (97.0%), mp 217°-219° C., $[\alpha]_D^{23} -17.6°$ (c=0.4 in DMF), $R_f^5$ 0.10.

Elemental analysis Calcd. for C₅₇H₉₅N₉O₁₄S₃: C, 55.81; H, 7.81; N, 10.28; S, 7.84. Found: C, 55.54; H, 7.82; N, 10.20; S, 7.82.

(6) Production of Boc-Ala-Met-Ala-Lys(Mtr)-Lys(Mtr)-Leu-Leu-NH₂[If]

Compound Ie (2.94 g) was treated with TFA (20 ml) for 30 min. The mixture was concentrated and the residue was triturated with ether to give a precipitate. The powder obtained was dissolved in DMF (20 ml) together with TEA (0.36 ml). Boc-Ala-ONB (0.84 g) was added and the whole was stirred for 6 h. The solution was concentrated and the residue was triturated with ether to give a precipitate, which was crystallized from MeOH-AcOEt: yield 2.90 g (96.0%), mp 227°-228° C., $[\alpha]_D^{23} -19.4°$ (c=0.3 in DMF), $R_f^5$: 0.10.

Elemental analysis Calcd. for C₆₀H₁₀₀N₁₀O₁₅S₃: C, 55.53; H, 7.77; N, 10.79; S, 7.41. Found: C, 55.55; H, 7.80; N, 10.70; S, 7.59.

(7) Production of Boc-Ala-Ala-Met-Ala-Lys(Mtr)-Lys(Mtr)-Leu-Leu-NH₂[Ig]

Compound If (2.6 g) was treated with TFA (20 ml) for 30 min and the resulting free base was coupled with Boc-ALA-ONB (0.77 g) in DMF (10 ml) for 6 h. The solution was concentrated, and the product was crystallized from MeOH: yield 2.45 g (89.4%), mp 243°-245° C., $[\alpha]_D^{23} -17.8°$ (c=0.4 in DMF), $R_f^1$ 0.50.

Elemental analysis Calcd. for C₆₃H₁₀₅N₁₁O₁₆S₃: C, 55.28; H, 7.73; N, 11.25; S, 7.03. Found: C, 55.28; H, 7.71; N, 11.20; S, 6.98.

(8) Production of Boc-Ile-Ala-Ala-Met-Ala-Lys(Mtr)-Lys(Mtr)-Leu-Leu-NH₂[I]

Compound Ig (2.0 g) was treated with TFA-anisole (20:1, 12 ml) for 30 min and the resulting product was dissolved in DMF (10 ml) together with TEA (0.23 ml) and then coupled with Boc-Ile-ONB (prepared from Boc-Ile-OH (0.46 g) for 10 h. The solution was concentrated and the residue was triturated with AcOEt to give a precipitate, which was washed with hot MeOH: yield 1.82 g (82.0%), mp 273°-274° C., $[\alpha]_D^{23} -15.6°$ (c=0.3 in DMF), $R_f^5$ 0.04, $R_f^1$ 0.73.

Elemental analysis Calcd. for C₆₉H₁₁₆N₁₂O₁₇S₃: C, 55.92; H, 7.89 N, 11.34; S. 6.49. Found: C, 55.61; H, 8.17; N, 11.33; S, 6.71.

(9) Production of Z-Lys(Mtr)-Gly-OBuᵗ[IIa]

Z-Gly-OBuᵗ (2.7 g) was hydrogenated in MeOH (100 ml) and the free base was coupled with Z-Lys(Mtr)-OH (prepared from the DCHA salt (6.6 g)) in the presence of HONB (2.0 g) and DCC (2.3 g) in acetonitrile (100 ml) for 6 h. After the usual work-up, the product was crystallized from pet. ether: yield 4.60 g (76.7%), mp 53°–56° C., $[\alpha]_D^{23} -8.4°$ (c=1.0 in MeOH), $R_f^5 0.42$.

Elemental analysis Calcd. for $C_{30}H_{43}N_3O_8S$: C, 59.48; H, 7.16; N, 6.94; S, 5.29. Found: C, 60.27; H, 7.39; N, 6.80; S, 5.04.

(10) Production of Z-Trp-Lys(Mtr)-Gly-OBu$^t$[IIb]

Compound IIa (3.63 g) was hydrogenated in MeOH (50 ml) and the free base was coupled with Z-Trp-ONB (3.0 g) in acetonitrile (50 ml). After the usual work-up, the product was crystallized from AcOEt-pet. ether: yield 4.30 g (90.5%), mp 120°–124° C., $[\alpha]_D^{23} -8.4°$ (c=0.3 in MeOH), $R_f^5 0.39$.

Elemental analysis Calcd. for $C_{41}H_{53}N_5O_9S$: C, 62.18; H, 6.75; N, 8.84; S, 4.05. Found: C, 62.47; H, 6.98; N, 9.04; S, 4.09.

(11) Production of Z-Asn-Trp-Lys(Mtr)-Gly-OBu$^t$-[IIc]

Compound IIb (3.96 g) was hydrogenated in MeOH (50 ml) and the resulting free base was coupled with Z-Asn-OH (1.33 g) in the presence of HONB (1.0 g) and DCC (1.2 g) in DMF (40 ml). The mixture was stirred for 10 h and concentrated to dryness. The residue was triturated with AcOEt-MeOH (5:2) to give a precipitate, which was washed with MeOH-acetonitrile (1:1): yield 3.96 g (87.4%), mp 200°–203° C., $[\alpha]_D^{23} -14.8°$ (c=0.5 in DMF), $R_f^1 0.44$.

Elemental analysis Calcd. for $C_{45}H_{59}N_7O_{11}S$: C, 59.65; H, 6.56; N, 10.82; S, 3.54. Found: C, 59.60; H, 6.48; N, 10.83; S, 3.80.

(13) Production of Mtr-Ile-Asn-Trp-Lys(Mtr)-Gly-OBu$^t$[II]

Compound IIc (2.70 g) was hydrogenated in DMF (60 ml) and the resulting free base was coupled with Mtr-Ile-OH prepared from the CHA salt (1.35 g) in the presence of HOBt (0.40 g) and DCC (0.68 g) in DMF. The mixture was stirred for 10 h, filtered and concentrated. The product was triturated with ether to give a precipitate, which was crystallized from hot MeOH to give needles: yield 2.93 g (95.8%), mp 207°–208° C., $[\alpha]_D^{23} -21.7°$ (c=0.3 in DMF), $R_f^1 0.61$.

Elemental analysis Calcd. for $C_{53}H_{76}N_8O_{13}S_2$: C, 58.00; H, 6.98; N, 10.21; S, 5.84. Found: C, 58.16; H, 7.14; N, 10.03; S, 5.93.

(14) Production of Mtr-Ile-Asn-Trp-Lys(Mtr)-Gly-Ile-Ala-Ala-Met-Ala-Lys(Mtr)-Lys(Mtr)-Leu-Leu-NH$_2$[III]

Compound II (1.02 g) was treated with TFA-anisole (10 ml–1 ml) at 20° C. for 30 min. After removal of the TFA by evaporation, the residue was triturated with ether to give a precipitate. Compound I (1.50 g) was also treated with TFA-anisole (10 ml–1 ml) at 20° C. for 30 min, and the resulting free base was coupled with the free acid obtained above in the presence of HONB (0.20 g) and DCC (0.25 g) in DMF (20 ml). The mixture was stirred for 10 h and concentrated to dryness. The residue was triturated with water to give a precipitate, which was further purified by washing with hot MeOH-AcOEt (1:1): yield 1.89 g (77.0%), mp 256°–259° C., $[\alpha]_D^{23} -8.6°$ (c=0.8 in DMF), $R_f^1 0.22$, $R_f^3 0.89$.

Elemental analysis Calcd. for $C_{113}H_{174}N_{20}O_{27}S_5 \cdot 2H_2O$: C, 55.60; H, 7.27; N, 11.48; S, 6.57. Found: C, 55.33; H, 7.30; N, 11.23; S, 6.65

(15) Production of H-Ile-Asn-Trp-Lys-Gly-Ile-Ala-Ala-Met-Ala-Lys-Lys-Leu-Leu-NH$_2$ (Mastoparan X)

Compound III (200 mg) was treated with 0.3 M MSA in TFA-thioanisole (9:1) (20 ml) at room temperature for 1 h. After addition of AcONH$_4$ (240 mg), the solution was concentrated and the residue was triturated with ether to give a precipitate. The powder obtained was dissolved in 1 N AcOH and passed through a column (2.2×120 cm) of Sephadex G-25 (1 N AcOH). The fractions (180–290 ml) were pooled and lyophilized. The product was dissolved in water and then passed through a column (1×10 cm) of Amberlite IRA-410 (acetate form). The eluates were applied to a column (2.2×17 cm) of carboxymethyl-cellulose, which was eluted with pH 6.8 ammonium acetate buffer (gradient: 0.005 M/0.6 M=400 ml/400 ml). The fractions (375–505 ml) containing the desired product were pooled and lyophilized. yield 60 mg (40%), $[\alpha]_D^{22} -63.5°$ (c=0.3 in 3% AcOH), $R_f^4$ (cellulose) 0.66, $R_f^6$ (cellulose) 0.64. Amino acid ratios in acid hydrolysate (4% thioglycolic acid in 6 N HCl): Lys 3.02(3); Trp 1.05(1); Asp 0.68(1); Gly 1.09(1); Val 3.26(3); Met 1.00(1); Ile 1.97(2); Leu 2.08(2); (average recovery 77%).

What we claim is:

1. A method of producing peptides having an ω-amino group, an α-amino group or both of said groups which comprises protecting the ω-amino group, the α-amino group or both of said groups in a starting compound containing said ω-amino group, α-amino group or both of said groups, subjecting the protected compound to a peptide synthesis reaction and removing the protective group or groups with an acid, the improvement wherein the protecting group is the 4-methoxy-2,3,6-trimethylbenzenesulfonyl group.

2. The method according to claim 1, wherein trifluoroacetic acid and/or methanesulfonic acid is used as the acid.

3. The method according to claim 1 or 2, wherein the protective group is eliminated in the presence of thioanisole.

4. In an amino acid or peptide or a salt thereof having an ω-amino group, an α-amino group or both of said groups protected, the improvement wherein the protected group is the 4-methoxy-2,3,6-trimethylbenzenesulfonyl group.

5. The amino acid according to claim 4, wherein the amino acid having a 4-methoxy-2,3,6-trimethylbenzenesulfonyl-protected ω-amino group and/or α-amino group is lysine derivative of the formula

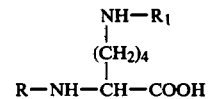

wherein at least one of R and R$_1$ is a 4-methoxy-2,3,6-trimethylbenzenesulfonyl group and the other, if any, is a hydrogen or a protective group other than a 4-methoxy-2,3,6-trimethylbenzenesulfonyl group.

* * * * *